(12) United States Patent
Nair et al.

(10) Patent No.: US 8,404,907 B2
(45) Date of Patent: Mar. 26, 2013

(54) PROCESS FOR CIS-1-CHLORO-3,3,3-TRIFLUOROPROPENE

(75) Inventors: Haridasan K. Nair, Williamsville, NY (US); Andrew Joseph Poss, Kenmore, NY (US); Rajiv Ratna Singh, Getzville, NY (US); Michael Van Der Puy, Amherst, NY (US); Ryan J. Hulse, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 159 days.

(21) Appl. No.: 13/030,789

(22) Filed: Feb. 18, 2011

(65) Prior Publication Data

US 2012/0215041 A1 Aug. 23, 2012

(51) Int. Cl.
- *C07C 21/00* (2006.01)
- *C07C 17/00* (2006.01)
- *C07C 19/08* (2006.01)
- *C07C 21/18* (2006.01)
- *C07C 23/00* (2006.01)
- *C07C 25/13* (2006.01)

(52) U.S. Cl. ......... 570/216; 570/123; 570/153; 570/175
(58) Field of Classification Search .............. None
See application file for complete search history.

(56) References Cited

U.S. PATENT DOCUMENTS

| 6,844,475 | B1 | 1/2005 | Tung et al. |
| 7,094,936 | B1 | 8/2006 | Owens et al. |
| 7,829,747 | B2 | 11/2010 | Wang et al. |
| 8,217,208 | B2 | 7/2012 | Hulse et al. |
| 2007/0027348 | A1 | 2/2007 | Quan et al. |
| 2010/0072415 | A1 | 3/2010 | Rao et al. |
| 2010/0145112 | A1 | 6/2010 | Ishihara et al. |

FOREIGN PATENT DOCUMENTS

WO 2010068715 6/2010

OTHER PUBLICATIONS

US 6,987,206, 01/2006, Owens et al. (withdrawn)

*Primary Examiner* — Sudhakar Katakam
*Assistant Examiner* — Clinton Brooks
(74) *Attorney, Agent, or Firm* — Bruce O. Bradford

(57) ABSTRACT

Disclosed is a process for making one isomer of $CF_3CH=CHCl$. More particularly, the invention comprises the production of $CF_3C\equiv CCl$ and its selective reduction to cis-1-chloro-3,3,3-trifluoropropene ($CF_3CH=CHCl$).

23 Claims, No Drawings

PROCESS FOR CIS-1-CHLORO-3,3,3-TRIFLUOROPROPENE

FIELD OF THE INVENTION

Disclosed is a process for making one isomer of CF₃CH=CHCl. More particularly, the invention comprises the production of CF₃C≡CCl and its selective reduction to cis-1-chloro-3,3,3-trifluoropropene (CF₃CH=CHCl).

BACKGROUND OF THE INVENTION

Trans-1-chloro-3,3,3-trifluoropropene (HCFC-1233zd E-isomer) has physical properties, including a boiling point of 20° C., which makes it attractive for certain applications such as foam blowing. The higher boiling point of the cis- or Z-isomer (bp 40° C.) makes it especially desirable not only for foam blowing applications but for solvent applications as well. However, the known procedures for making HCFC-1233zd, all afford only the trans-isomer. Currently there is no known procedure for making exclusively or even primarily the cis-isomer.

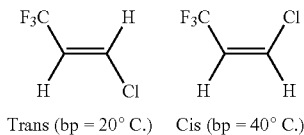 [SMILES: FC(F)(F)/C=C/Cl ; FC(F)(F)/C=C\Cl]

Trans (bp = 20° C.)   Cis (bp = 40° C.)

Although, the formation of cis-CF₃CH=CHCl is reported by Kamil et al., Inorg. Chemistry, 1986, 25, 3760, the product in fact is the trans-isomer—as confirmed by NMR spectroscopy and boiling point. Similarly, dehydrofluorination of 3-chloro-1,1,1-trifluoro-3-iodopropane was reported by Hazeldine, J. Chem. Soc., 1953, 1199-1204, to afford cis-1-chloro-3,3,3-trifluoroprpene, but again, the actual product is the trans isomer with a boiling point of 20° C.

Thus, there continues to be a need for a suitable process to make the cis-isomer of 1-chloro-3,3,3-trifluoropropene for use in various applications. The present invention meets that need.

SUMMARY OF THE INVENTION

Disclosed is a process for making the cis isomer of CF₃CH=CHCl. More particularly, the invention comprises the selective reduction of CF₃C≡CCl to cis-1-chloro-3,3,3-trifluoropropene (CF₃CH=CHCl).

One embodiment of the invention is a process for making cis-1-chloro-3,3,3-trifluoropropene comprising the steps of;
(a) providing 1-chloro-3,3,3-trifluoropropyne and
(b) reducing the 1-chloro-3,3,3-trifluoropropyne to afford cis-1-chloro-3,3,3-trifluoropropene.

Reaction Step (a)

In certain embodiments, the 1-chloro-3,3,3-trifluoropropyne is provided by reacting CF₃CCl=CHCl (HCFC-1223xd) with a base in the presence of a phase transfer catalyst. The base employed is an aqueous base. One preferred embodiment comprises KOH. One preferred phase transfer catalyst comprises the quaternary ammonium salt composition commercially known as Aliquat 336. Other phase transfer catalysts may be selected from the group consisting of tetra-alkyl ammonium salts, phosphonium salts, crown ethers, and mixtures thereof.

In certain embodiments, the 1-chloro-3,3,3-trifluoropropyne is provided by reacting CF₃CH=CCl₂ with a base in the presence of a phase transfer catalyst. The base employed is an aqueous base. One preferred embodiment comprises KOH. One preferred phase transfer catalyst comprises Aliquat 336. Other phase transfer catalysts may be selected from the group consisting of tetra-alkyl ammonium salts, phosphonium salts, crown ethers, and mixtures thereof.

In certain embodiments, the 1-chloro-3,3,3-trifluoropropyne is provided by reacting CF₃CH₂CCl₃ with a base in the presence of a phase transfer catalyst. The base employed is an aqueous base. One preferred embodiment comprises KOH. One preferred phase transfer catalyst comprises Aliquat 336. Other phase transfer catalysts may be selected from the group consisting of tetra-alkyl ammonium salts, phosphonium salts, crown ethers, and mixtures thereof.

Reaction Step (b)

In the second step of the reaction, the 1-chloro-3,3,3-trifluorpropyne is reduced to afford cis-1-chloro-3,3,3-trifluoropropene, preferably in high yield with little or no trans isomer formed.

One preferred reducing agent is hydrogen. Another preferred reducing agent is a hydrogen generating substance. Reduction typically takes place in the presence of a catalyst. One catalyst comprises a nickel catalyst. Another catalyst comprises a borane catalyst.

A preferred catalyst comprises a palladium catalyst that has been poisoned to prevent over-reduction. In some embodiments the palladium catalyst has been poisoned with lead. In some embodiments the palladium catalyst has been poisoned with quinoline. In some embodiments the palladium catalyst has been poisoned with KOH.

An especially preferred palladium catalyst comprises the Lindlar catalyst. One commercial source for the Lindlar catalyst is the Aldrich Chemical Company which sells 5% Pd on calcium carbonate poisoned with lead. When the Lindlar catalyst is used, the reduction takes place at a temperature in the range of from about 0° C. to 20° C. When the Lindlar catalyst is used, the reduction takes place over a reaction time of from 24 to 48 hours. When the Lindlar catalyst is used, the hydrogen pressure is less than about 150 psi (about 1000 KPa). Other catalysts, such as Nanoselect LF (Strem Chemicals, Inc.) may be used instead of the Lindlar catalyst.

DETAILED DESCRIPTION OF THE INVENTION

The present invention describes a two step process for making cis-1-chloro-3,3,3-trifluoropropene. In the first step, 1-chloro-3,3,3-trifluoroproyne, CF₃C≡CCl, is prepared from a suitable starting material, and is then reduced to afford cis-1-chloro-3,3,3-trifluoropropene (cis-CF₃CH=CHCl).

One method to prepare CF₃C≡CCl is from the reaction of CF₃CH₂CH₂Cl with chlorine followed by successive dehydrohalogenations as reported in the Russian Patent No. SU169522.

The reaction of cupric chloride and zinc derivative of 3,3,3-trifluoropropyne in HCONMe₂ gives 1-chloro-3,3,3-trifluorproyne as a by-product in very low yield as described in J. Org. Chemistry (1966), 31(10), 3292-3295.

Another way to make 1-chloro-3,3,3-trifluoropropyne is from CF₃CCl=CHCl (HCFC-1223xd), as follows. Slow addition (over 1 to 3 hrs) of a base (e.g., aqueous KOH) to HCFC-1223xd in the presence of a phase transfer catalyst such as Aliquat 336 at 40° C. to 45° C. affords 1-chloro-3,3,3-trifluorpropyne (CF₃C≡CCl) in good yield. This is somewhat surprising since, in general, one would expect the hydrolysis of $CF_3CCl=CHCl$ with a base to afford products such as an aldehyde or ketone rather than a dehydrochlorination product.

Other raw materials including $CF_3CH=CCl_2$ or $CF_3CH_2CCl_3$ can also be used for producing 1-chloro-3,3,3-trifluorpropyne. Phase transfer catalysts such as tetra-alkyl ammonium salts, phosphonium salts, crown ethers, and the like, are also suitable for dehydrochlorination. The temperature range for this reaction is from about 20° C. to 50° C. Purification to a large extent is done by passing the effluent (mainly the 1-chloro-3,3,3-trifluorpropyne and starting material) through a water condenser at a temperature range of from about 5° C. to 15° C. Further purification is achieved by distillation.

In the second step of the reaction, 1-chloro-3,3,3-trifluoropropyne is reduced to give the desired cis-1-chloro-3,3,3,trifluoropropene (cis-$CF_3CH=CHCl$). This can be accomplished with hydrogen or a hydrogen generating substance in the presence of a nickel catalyst or a palladium catalyst that has been suitably poisoned to prevent over-reduction. Certain boranes can also be used but these tend to be far more expensive and may thus be unacceptable for large scale operations. The palladium catalyst may be "poisoned" with lead, quinoline, or KOH.

A convenient Pd catalyst is the Lindlar catalyst. Reductions with this catalyst can be run at a temperature in the range of from about 0° C. to 20° C. without any solvent to afford cis-$CF_3CH=CHCl$, with no trans-isomer being observed. Reaction times are typically from 24 to 48 hours with this catalyst at hydrogen pressures less than about 150 psi (about 1000 KPa). Solvents such as ethanol or methanol can also be used. However, processes without solvent are preferred to reduce waste and improve productivity. Commercially available Lindlar catalysts can be employed. Purification can be accomplished by distillation. Depending on the reaction conditions, by-products may include $CF_3CH=CH_2$ and $CF_3CH_2CH_3$.

The identity of the cis isomer was determined by analytical data—GC-MS, boiling points and NMR. In the $^{19}F$ and $^1H$ NMR spectra, chemical shifts ($\delta$) are distinctly different for the cis and trans isomers of 1-chloro-3,3,3,trifluoropropene as reported (see Journal of Fluorine Chemistry, 128 (2007) 190-195).

EXAMPLES

Example 1

Preparation of 1-chloro-3,3,3-trifluoropropyne ($CF_3C\equiv CCl$) by the Dehydrohalogenation of HCFC-1223xd To a 2.0 L three necked flask equipped with a liquid addition pump, temperature probe and two water condensers at 5° C. to 15° C. (Note: a Graham condenser may also be used) and a dry ice condenser in series connected to a nitrogen tee was charged with $CF_3CCl=CHCl$ (HCFC-1223xd; 297 g, 1.81 mol) and 10 mL of Aliquat®336. This solution was heated to and maintained at 40° C. to 45° C. and 400 mL aq. KOH solution (containing 1.81 mole of KOH) was added with the addition pump over a period of 3 hours. After complete addition of KOH solution, the reaction mixture was heated at 45° C. to 50° C. for an additional hour. The dry ice trap was brought to room temperature and weighed. The product (207 g; 90% yield), 1-chloro-3,3,3-trifluoropropyne, was collected in the dry ice trap. Purity ranged from 94% to 98%; further purification was accomplished by distillation; bp=3° C. to 4° C.; GC purity>98%; GC/MS: m/e at 128/130 for M+; (M=$C_3ClF_3$).

Example 2

Preparation of cis-1-chloro-3,3,3-trifluoropropene by the Reduction of 1-chloro-3,3,3-trifluoropropyne To a clean, dry and leak tested 450 mL Parr® Reactor was added 4.0 g Lindlar™ catalyst (5% Pd on calcium carbonate poisoned with lead, obtained from Aldrich Chemical Co). The reactor was cooled with dry ice, evacuated and 80.3 g (0.62 mol) of 1-chloro-3,3,3-trifluoropropyne was condensed in. The temperature was brought to and maintained at from about 5° C. to 15° C. Hydrogen was charged to 150 psig. Additional hydrogen was charged after the pressure dropped to 80 to 50 psig. A total of 0.62 mol of $H_2$ gas was added for the reduction. The reaction was run until 0.8 to 1 equivalents of $H_2$ had been added. In addition to some un-reacted starting material, other materials identified in the reaction mixture were $CF_3CH=CH_2$ and $CF_3CH_2CH_3$ (in about a 4:2 ratio).

Excess hydrogen from the reactor was bled after cooling it to about 0° C., and the volatile product was flash distilled into a metal cylinder by raising the temperature to from about 20° C. to 50° C. The product (63.4 g) was distilled (bp 40° C. to 41° C.) to afford 30 g of cis-$CF_3CH=CHCl$. The yield of cis-$CF_3CH=CHCl$ was 52%. Analytical data were consistent with the cis-isomer. GC/MS:130/132 for M+; $^{19}F$ NMR (CDCl3) $\delta$-60.5 (d) ppm, J=7.2 Hz; $^1H$(CDCl3) $\delta$=6.6 (d) (J=8.5 Hz), 6.1 (dq) (J=8.3 and 7.3 Hz) ppm.

Example 3

Preparation of cis-1-chloro-3,3,3-trifluoropropene by the Reduction of 1-chloro-3,3,3-trifluoropropyne in Ethanol To a clean, dry and leak tested 450 mL Parr® Reactor was added 4.0 g Lindlar™ catalyst (5% Pd on calcium carbonate poisoned with lead, obtained from Aldrich Chemical Co.) followed by 50 mL ethanol under nitrogen purge. The reactor was cooled to about −30° C., evacuated and 65 g 1-chloro-3,3,3-trifluoropropyne was condensed in. The temperature was brought to and maintained at from about 5° C. to 10° C. and reactor was charged with hydrogen to 160 psig. Additional hydrogen was charged after the pressure dropped to about 50 to 70 psig. A total of 0.51 moles of $H_2$ was added over 48 hrs. Analysis of gas phase material in the reactor indicated the same materials as in Example 1. Excess hydrogen was bled off after cooling the reactor to −10° C. The cold reaction mixture was filtered under nitrogen pressure and the filtrate was analyzed by GC, which indicated cis $CF_3CH=CHCl$ and unreacted $CF_3C\equiv CCl$ as the major products besides solvent ethanol. The cold filtrate was poured into cold water (about 0° C.) and the lower layer (20 g) of crude cis-$CF_3CH=CHCl$ was separated.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for making cis-1-chloro-3,3,3-trifluoropropene comprising the steps of a) providing 1-chloro-3,3,3-trifluoropropyne and b) reducing the 1-chloro-3,3,3-trifluoropropyne to afford cis-1-chloro-3,3,3,trifluoropropene.

2. The process of claim 1, wherein the 1-chloro-3,3,3-trifluoropropyne is provided by reacting $CF_3CCl=CHCl$ (HCFC-1223xd) with an alkali metal hydroxide.

3. The process of claim 2, wherein the alkali metal is selected from Group IA of the Periodic Table of the Elements.

4. The process of claim 3, wherein the alkali metal is selected from lithium, sodium and potassium.

5. The process of claim 4, wherein the alkali metal hydroxide is an aqueous composition.

6. The process of claim 5, wherein a phase transfer catalyst is used.

7. The process of claim 1, wherein the 1-chloro-3,3,3-trifluoropropyne is provided by reacting $CF_3CH=CCl_2$ with an aqueous KOH in the presence of a phase transfer catalyst.

8. The process of claim 7, wherein the phase transfer catalysts is selected from the group consisting of tetra-alkyl ammonium salts, phosphonium salts and crown ethers.

9. The process of claim 1, wherein the 1-chloro-3,3,3-trifluoropropyne is provided by reacting $CF_3CH_2CCl_3$ with a base in the presence of a phase transfer catalyst.

10. The process of claim 9, wherein the phase transfer catalysts is selected from the group consisting of tetra-alkyl ammonium salts, phosphonium salts and crown ethers.

11. The process of claim 1, wherein the 1-chloro-3,3,3-trifluorpropyne is reduced with hydrogen.

12. The process of claim 11, wherein the reduction takes place in the presence of a nickel catalyst.

13. The process of claim 11, wherein the reduction takes place in the presence of a palladium catalyst that has been poisoned to prevent over-reduction.

14. The process of claim 13, wherein the palladium catalyst has been poisoned with lead.

15. The process of claim 13, wherein the palladium catalyst has been poisoned with quinoline.

16. The process of claim 13, wherein the palladium catalyst has been poisoned with KOH.

17. The process of claim 13, wherein the palladium catalyst comprises the Lindlar catalyst.

18. The process of claim 17, wherein the reduction takes place at a temperature in the range of from about 0° C. to 20° C.

19. The process of claim 18, wherein the reduction takes place over a reaction time of from 24 to 48 hours.

20. The process of claim 19, wherein the hydrogen pressure is less than about 150 psi (about 1000 KPa).

21. The process of claim 1, wherein the 1-chloro-3,3,3-trifluorpropyne is reduced with a hydrogen generating substance.

22. The process of claim 11, wherein the reduction takes place in the presence of the NanoSelect LF catalyst.

23. The process of claim 11, wherein the reduction takes place in the presence of a borane catalyst.

* * * * *